(12) United States Patent
Hely

(10) Patent No.: US 7,252,647 B1
(45) Date of Patent: Aug. 7, 2007

(54) SELF TIGHTENING, ANKLE BRACE

(75) Inventor: John P. Hely, Oxnard, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 604 days.

(21) Appl. No.: 10/753,280

(22) Filed: Jan. 9, 2004

(51) Int. Cl.
*A61F 13/06* (2006.01)
*A61F 13/00* (2006.01)
*A61F 5/37* (2006.01)

(52) U.S. Cl. .......................... 602/65; 602/60; 128/882

(58) Field of Classification Search .................. 602/23, 602/27, 65, 60–62; 128/877–882; 2/455, 2/22, 908, 912, 917, 16
See application file for complete search history.

(56) References Cited

U.S. PATENT DOCUMENTS 6,447,469 B1 *   9/2002   Ritchie ...................... 602/27

\* cited by examiner

*Primary Examiner*—Patricia Bianco
(74) *Attorney, Agent, or Firm*—William W. Haefliger

(57) ABSTRACT

A self tightening, ankle brace, comprising combination, strap structure including first and second elongated strap portions, said structure defining a through slit, said first portion adapted to be wrapped about an ankle or lower leg, said second portion adapted to extend through the slit then downwardly at one side of the ankle, then underfoot, and then upwardly at the opposite side of the ankle, in operative attachment and said first portion.

12 Claims, 3 Drawing Sheets

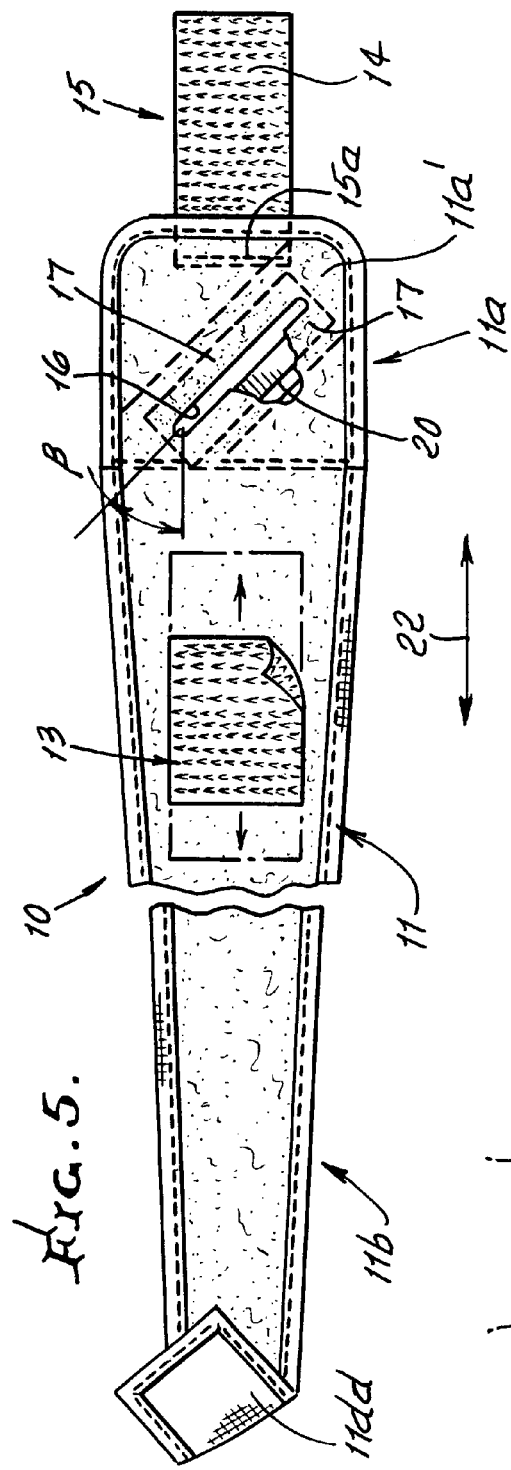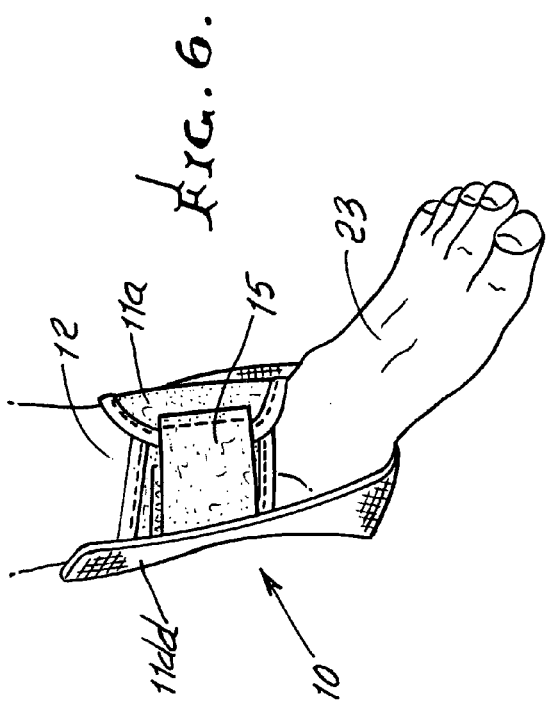

SELF TIGHTENING, ANKLE BRACE

BACKGROUND OF THE INVENTION

This invention relates generally to ankle braces, and more particularly to improvements in such braces enabling ease and rapidity of application to the wearer's ankle, as well as continued and enhanced ankle stability, due to brace self-tightening.

Injuries to ankles such as sprains frequently require the application of ankle braces, which must be repeatedly applied and removed at frequent intervals. Accordingly, ease and rapidity of application and removal are essential. There is need for improvements in ankle braces enabling such ease and rapidity of brace application and removal, as well as providing for enhanced and/or continued ankle stability, when applied.

SUMMARY OF THE INVENTION

It is a major object of the invention to provide an improved ankle brace meeting the above need. Basically, the ankle brace apparatus embodying the invention comprises:

a) strap structure including first and second elongated strap portions, said structure defining a through slit, b) said first portion adapted to be wrapped about an ankle, c) said second portion adapted to extend through the slit, then downwardly at one side of the ankle, then underfoot, and then upwardly at the opposite side of the ankle, for operative attachment to said first portion.

As will appear, stabilized and simplified support at ankle opposite sides with self adjustment, an important, along with provision of a unitary strap configuration. As will be seen, the unitary strap incorporate said first and second portions, the second portion foldable relative to the first portion, and proximate the slit that accommodates self adjustment. The slit typically extends at angle $\alpha$ relative to the strap first portion direction of elongation, where $$40° < \alpha < 50°.$$

A further object of the invention is to provide an adjustable hook and pile interconnection that defines the attachment between the strap first and second portions.

The method of establishing the brace in operation position includes the steps a) and providing strap structure including first and second elongated strap portions, said structure defining a through slit, b) wrapping the strap first portion about the lower leg above the malleolus, and passing the strap second portion through the slit, and to extend downwardly at the ankle side.

As will be seen, the strap second portion is allowed to self adjustingly slide endwise in said slit, in response to ankle flexing, assisting tightening of strap structure.

Another step of the method may be considered to include folding of the strap structure to direct the strap downwardly through an angled slit that extends at an angle $\alpha$ relative to the strap first portion direction of elongation, where $$40° < \alpha < 50°.$$

These and other objects and advantages of the invention, as well as the details of an illustrative embodiment, will be more fully understood from the following specification and drawings, in which:

DRAWING DESCRIPTION

FIG. 5 is a plan view of the FIG. 1 strap showing its outer side, in flattened position; and FIG. 6 is like FIG. 1, but showing a mirror image strap applied to the wearer's left foot.

DETAILED DESCRIPTION

Figure 3:
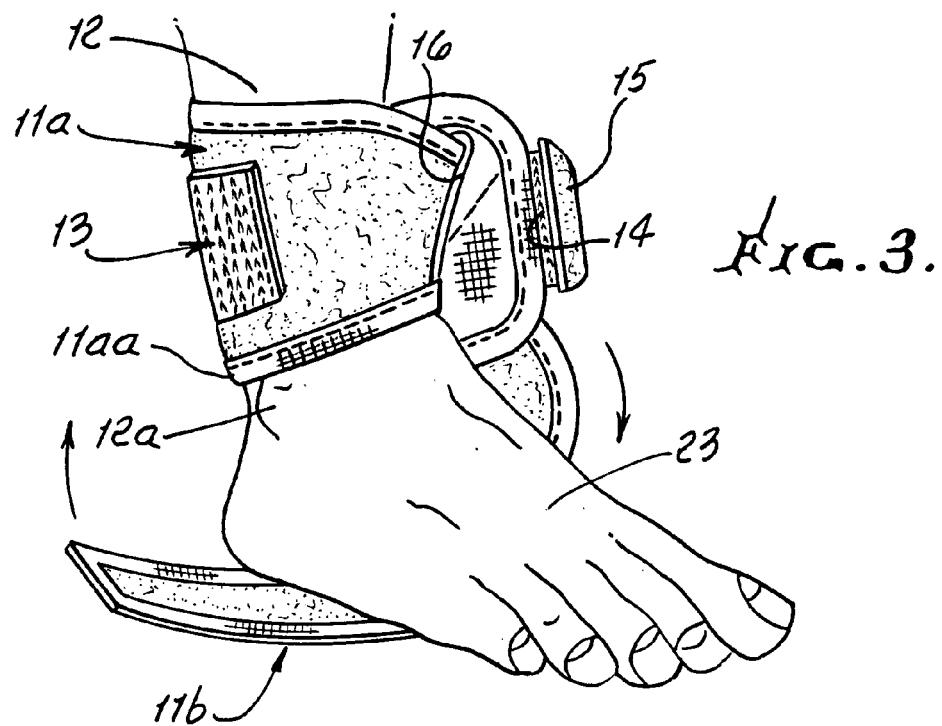
FIG. 3 is a right side perspective view showing the FIG. 1 strap in partially applied position.
Figure 4:
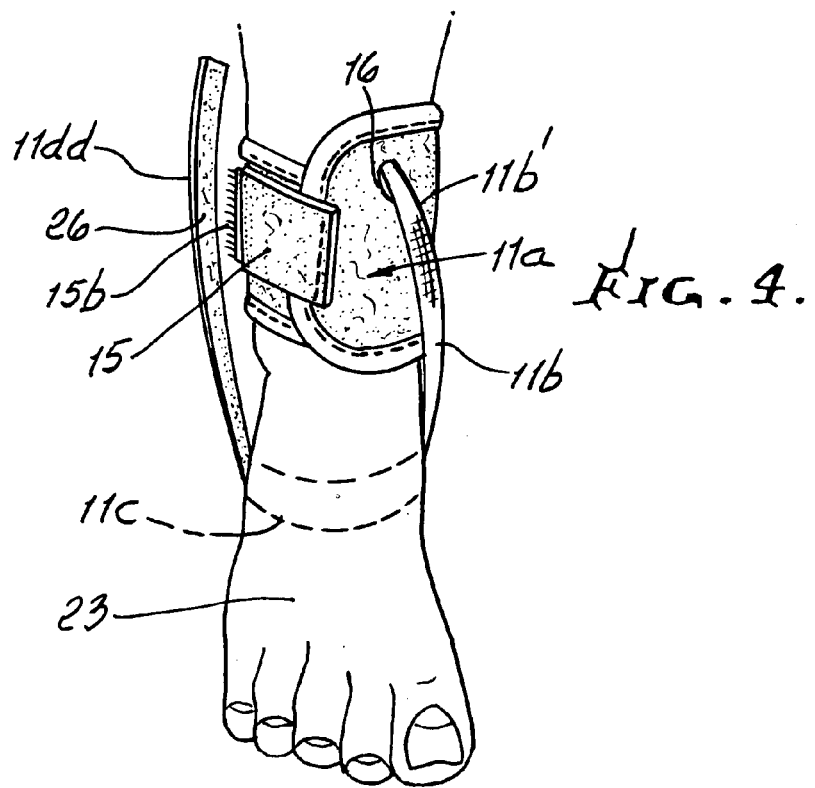
FIG. 4 is a frontal view showing the FIG. 1 strap in partially applied position.

In the drawings, the brace 10 includes an elongated strap structure 11 having first 11a and second 11b strap portions. First portion 11a is configured to wrap about the lower leg 12, just above the protruding malleolus region 12a, which blocks the wrap from shifting downwardly. See in FIG. 3 lower edge beading 11aa of the strap first portion retained just above the protrusion 12a at the user's right ankle. The wrapped first portion 11a is initially fixed in position by an attachment means, one example being hook and pile (VEL-CRO) elements shown at 13 on the outer side of 11a, and at 14 on the inner side of a tab or flap 15 attached at 15a to the end of 11a.

The strap portion 11a also has, or defines, an associated "re-direction means", as for example an angled slit or slot 16 extending through 11a near its end 11a', to which flap 15 is attached.

Stiffener means may be provided proximate the inner side of 11a, proximate slit 16, to stiffen the re-directing function of the slit i.e. re-directing of the strap second portion 11b to extend downwardly through the slit, and as accommodated by down folding at 11b' of the strap 11, after passing through the slit. See FIG. 2.

Lengthwise elongated cushioned areas 17, extend at opposite sides of the concealed elongated stiffeners 20. The stiffeners which may be defined by thin metallic members, extend generally diagonally and parallel to the slit, at angle $\beta$ relative to the length direction 22 of the strap, where $\beta$ is between 30° and 60°, and preferably about 45°.

Figure 2:
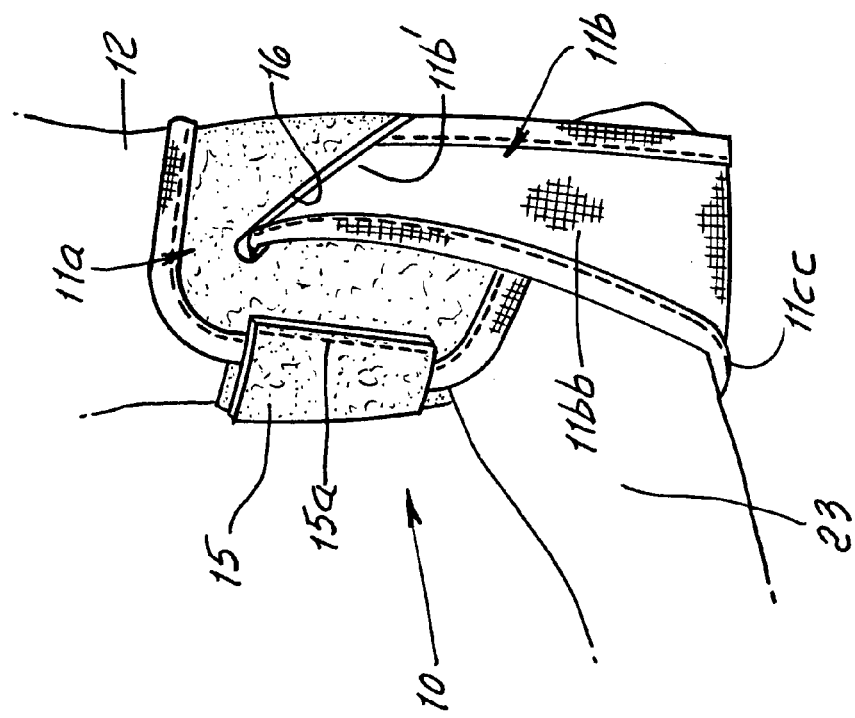
FIG. 2 is a left side elevation of the strap seen in FIG. 1.
Figure 1:
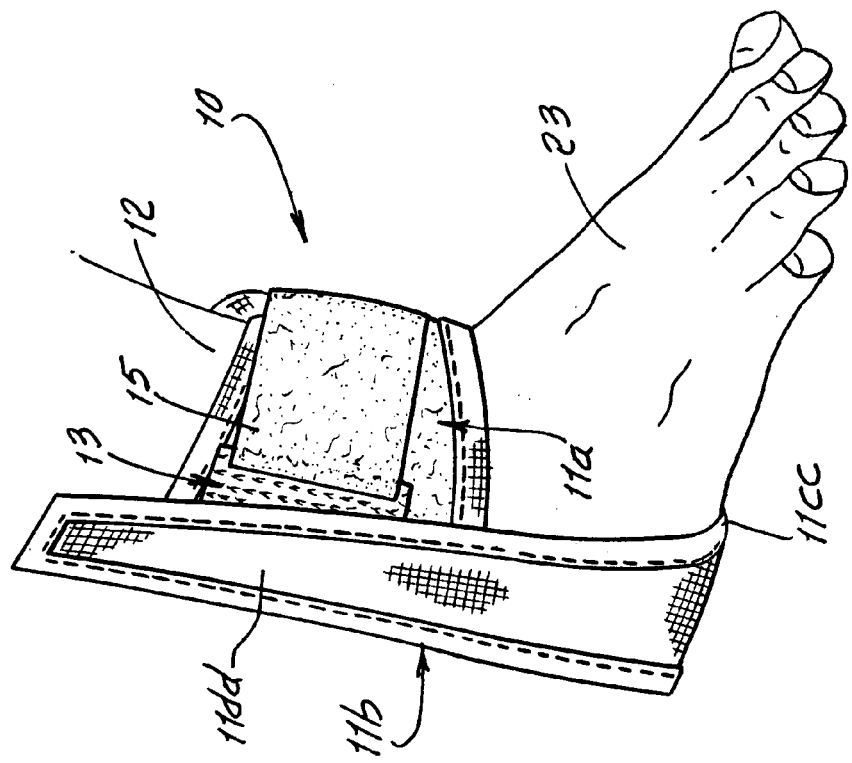
FIG. 1 is a right side elevation showing a preferred strap, applied to an ankle region of a right foot.

FIGS. 1 and 2 show the strap portion 11b extending downwardly at 11bb at one side of the ankle (preferably the inner side); then extending under the foot 23, at 11cc; and then extending upwardly at 11dd at the outer side of the foot, for easy attachment to strap portion 11a. The strap extent 11dd may cover the malleolus, when pulled up into affixing position defined by adjusted hook and pile elements as at 15b and 26 on the two strap portions 11a and 11b. The latter may be used to easily and adjustably attach the strap portion 11dd to the wrap, allowing self-adjusting or self tightening of the brace, as also accommodated by adjusting of the folded strap portion 11b' at the slit. Removal of the brace is quick, as enabled by pulling 11dd free from the wrap.

The method of strap use includes:

a) providing strap structure including first and second elongated strap portions, said strap first portion extending in a generally longitudinal direction, said structure defining a through slit, extending through the strap first portion at an angle $\alpha$ between 40° and 50° relative to said longitudinal direction, b) wrapping the strap first portion about a leg just above or proximate the malleolus, c) passing said strap second portion through the slit and then folding it to extend downwardly at one side of the ankle, then underfoot, and then upwardly at the opposite side of the ankle, in operative attachment with said first portion.

The method also include allowing the strap second portion to self adjustingly slide endwise in the slit, in response to ankle flexing, assisting tightening of the strap structure; and folding of the strap structure to cause the strap second portion to extend downwardly through the slit.

I claim:

1. A self tightening, ankle brace, comprising combination,
   a) strap structure including first and second elongated strap portions, said strap first portion extending in a generally longitudinal direction, said structure defining a through slit extending diagonally through the strap first portion at an angle α between 40° and 50° relative to said longitudinal direction,
   b) said strap first portion adapted to be wrapped about an ankle,
   c) said strap second portion extending through the strap first portion via the slit, and folded at the slit to extend downwardly and normal to said longitudinal direction and at one side of the ankle, then underfoot, and then upwardly at the opposite side of the ankle, for operative attachment with said first portion.

2. The combination of claim 1 wherein the second portion is folded relative to the first portion, proximate the slit.

3. The combination of claim 2 wherein the slit extends linearly entirely through the strap first portion and at said angle α relative to the strap first portion direction of elongation, there being hook or pile fasteners on the strap and between which the slit is located.

4. The combination of claim 1 wherein said structure forms a unitary strap incorporating said first and second portions.

5. The combination of claim 1 including stiffener means on the first strap portion and proximate the slit, said means including elongated stiffeners extending parallel to the slit and at opposite sides thereof, with cushioning at the stiffeners.

6. The combination of claim 1 including an adjustable hook and pile connection defining said attachment.

7. The method of establishing a self tightening ankle brace in operative position which includes
   a) providing strap structure including first and second elongated strap portions, said strap first portion extending in a generally longitudinal direction, said structure defining a through slit extending through the strap first portion at an angle α between 40° and 50° relative to said longitudinal direction,
   b) wrapping the strap first portion about a leg just above or proximate the malleolus,
   c) passing said strap second portion through the slit and with folding at or proximate the slit to extend downwardly at one side of the ankle, then underfoot, and then upwardly at the opposite side of the ankle, in operative attachment with said first portion.

8. The method of claim 7 including operatively attaching the strap second portion to the strap first portion via hook and pin elements to tighten the strap second portion under foot.

9. The method of claim 7 including allowing the strap second portion to self adjustingly slide endwise in said slit, in response to ankle flexing, assisting tightening of the strap structure.

10. The method of claim 7 including forming said slit to extend linearly at said angle α relative to the strap first portion direction of elongation, and providing hook or pile fasteners on the strap and between which the slit is located.

11. The method of claim 7 including folding the strap structure to cause the strap second portion to extend downwardly through the slit.

12. The method of claim 7 including providing stiffener means on the first strap portion and proximate the slit, said means provided to include elongated stiffeners extending parallel to the slit and at opposite sides thereof, and providing cushioning to extend over said stiffeners.

* * * * *